(12) United States Patent
Guelzow et al.

(10) Patent No.: US 7,631,760 B2
(45) Date of Patent: Dec. 15, 2009

(54) DUAL COMPARTMENT POUCH

(75) Inventors: David Guelzow, Circle Pines, MN (US); Adam Dworak, Northbrook, IL (US); Chris Heezen, Arlington Heights, IL (US); Jose Gutierrez, Mundelein, IL (US)

(73) Assignee: Amcor Flexibles Healthcare, Inc., Mundelein, IL (US)

( * ) Notice: Subject to any disclaimer, the term of this patent is extended or adjusted under 35 U.S.C. 154(b) by 126 days.

(21) Appl. No.: 12/027,575

(22) Filed: Feb. 7, 2008

(65) Prior Publication Data
US 2009/0200198 A1 Aug. 13, 2009

(51) Int. Cl.
*A61B 17/06* (2006.01)

(52) U.S. Cl. ............... 206/438; 206/204; 206/439; 206/484; 206/484.1; 383/38; 383/102; 53/425; 53/434

(58) Field of Classification Search ............... 206/571, 206/438, 439, 484, 484.1, 204; 383/38, 101, 383/102, 103; 53/425, 434; 422/26, 27, 422/58
See application file for complete search history.

(56) References Cited

U.S. PATENT DOCUMENTS

| | | | | |
|---|---|---|---|---|
| 3,403,776 | A | * | 10/1968 | Denny .................... 206/363 |
| 3,754,700 | A | * | 8/1973 | Bonk ...................... 206/439 |
| 3,761,013 | A | | 9/1973 | Schuster |
| 3,762,404 | A | * | 10/1973 | Sakita ....................... 602/6 |
| 3,939,971 | A | | 2/1976 | Tulis |
| 4,057,144 | A | | 11/1977 | Schuster |
| 4,418,055 | A | | 11/1983 | Andersen et al. |
| 4,660,721 | A | | 4/1987 | Mykleby |
| 4,714,595 | A | * | 12/1987 | Anthony et al. ............ 422/294 |
| 4,813,210 | A | | 3/1989 | Masuda et al. |
| 4,920,105 | A | | 4/1990 | Zelman |
| 5,342,673 | A | | 8/1994 | Bowman et al. |
| 5,551,781 | A | | 9/1996 | Wilkes et al. |
| RE36,071 | E | * | 2/1999 | Heacox ..................... 206/210 |

(Continued)

FOREIGN PATENT DOCUMENTS

DE 37 17 916 12/1988

(Continued)

OTHER PUBLICATIONS

European Search Report for EP 09152197.1, dated May 28, 2009.

*Primary Examiner*—David T Fidei
(74) *Attorney, Agent, or Firm*—Alston & Bird LLP

(57) ABSTRACT

The invention provides a dual compartment pouch having first and second compartments that are separated from each other by an impervious inner sheet having a breathable membrane. The breathable membrane comprises a breathable material that is pervious to moisture and gases, and impervious to liquids as well as microorganisms. The breathable membrane allows a sterilizing gas to be introduced between the first and second compartments. The front and back sheets are sealed to the inner sheet to define the first and second compartments in which the inner sheet forms a common wall between the compartments. The breathable membrane is disposed towards a central portion of the inner sheet and is spaced apart from the seams joining the front and back sheets to the inner sheet. In one embodiment, a sterilized article is disposed in one compartment, and an absorbent packets are disposed in the other compartment.

24 Claims, 8 Drawing Sheets

U.S. PATENT DOCUMENTS

| | | | |
|---|---|---|---|
| 5,868,244 | A | 2/1999 | Ivanov et al. |
| 5,947,288 | A | 9/1999 | Dykstra et al. |
| 5,964,261 | A | 10/1999 | Neuenfeldt et al. |
| 6,021,625 | A | 2/2000 | Cerwin et al. |
| 6,024,683 | A | 2/2000 | Wilkes |
| 6,059,112 | A | 5/2000 | Dykstra et al. |
| 6,065,597 | A | 5/2000 | Pettersson et al. |
| 6,098,800 | A | 8/2000 | Bennish, Jr. et al. |
| 6,234,310 | B1 | 5/2001 | Goldhaber |
| 6,279,745 | B1 | 8/2001 | Huynen et al. |
| 6,412,639 | B1 | 7/2002 | Hickey |
| 6,503,183 | B1 | 1/2003 | Bennish, Jr. et al. |
| 6,594,971 | B1 | 7/2003 | Addy et al. |
| 6,915,623 | B2 | 7/2005 | Dey et al. |
| 6,945,017 | B1 | 9/2005 | Bonney et al. |
| 6,986,730 | B1 | 1/2006 | Hoekstra |
| 7,000,770 | B2 | 2/2006 | Clarke et al. |
| 7,040,485 | B2 * | 5/2006 | Gupta et al. ............. 206/484.1 |
| 2004/0068293 | A1 | 4/2004 | Scalzo et al. |
| 2004/0068294 | A1 | 4/2004 | Scalzo et al. |
| 2005/0101993 | A1 | 5/2005 | Scalzo et al. |
| 2006/0010841 | A1 | 1/2006 | Trezza, II et al. |
| 2006/0091034 | A1 | 5/2006 | Scalzo et al. |
| 2006/0091035 | A1 | 5/2006 | Scalzo et al. |
| 2006/0260967 | A1 | 11/2006 | Clarke et al. |

FOREIGN PATENT DOCUMENTS

| | | |
|---|---|---|
| EP | 0 846 445 | 6/1998 |
| EP | 0 700 319 | 6/2000 |
| EP | 1 520 795 | 4/2005 |
| WO | WO 91/11374 | 8/1991 |
| WO | WO 2004/066876 | 8/2004 |
| WO | WO 2004/071308 | 8/2004 |
| WO | WO 2005/073091 | 8/2005 |
| WO | WO 2006/063050 | 6/2006 |

* cited by examiner

DUAL COMPARTMENT POUCH

FIELD OF THE INVENTION

The present invention is directed to a pouch for sterilizing articles, and more particularly, a multicompartment pouch for containing an article and absorbent packets separate from each other.

BACKGROUND OF THE INVENTION

A variety of different stents for use in angioplasty procedures have been developed in which a therapeutic drug agent is coated onto the stent prior to use. In particular, coated stents have been developed that include therapeutic drug agents that are intended to help prevent renarrowing of the arteries, also known as restenosis, after an angioplasty procedure has been performed.

Generally, the stents are precoated with the therapeutic drug agents prior to packaging of the stent and its associated catheter delivery system so that the stent can be removed from its package and used directly in a procedure. However, treated stents often present problems associated with drug administration because of the presence of the therapeutic drug agent. For example, for a drug to be administered effectively, the integrity of the active component of the drug as well as the drug's effective dosage should be maintained. Certain drugs may be adversely affected by reacting with various gases that may be found in the atmosphere of the package, such as oxygen, moisture vapor, and the like. As a result, it is generally desirable to control and/or minimize the level of such gases in the package.

Additionally, it is necessary to sterilize the treated stents during the packaging process. Common forms of sterilization include irradiation; autoclaving, and treatment with a sterilizing gas, such as ethylene oxide. Typically, treatment with a sterilizing gas is used to sterilize treated stents. One of the most common forms of sterilizing such stents involves a multi-step process in which the treated stent is first placed in a flexible packaging bag formed of a breathable material, such as paper or a nonwoven sheet material, such as Tyvek®. This packaging bag along with the stent is then treated with a sterilizing gas. Thereafter the packaging bag and the stent are placed into an outer bag comprising a barrier film. The treated stent and the packaging bag are then typically sealed in the barrier bag until removed for use. Such a packaging process is typically undesirable because it requires multiple steps and two separate and distinct packaging bags. Other packaging systems for coated stents have typically comprised a thermoform tray insert in a foil pouch, or a thermoform tray having a barrier lid in a foil pouch, into which the stent is vacuum packed.

Such conventional packaging for stents generally does not provide for sufficient control of gases in the package. Without such appropriate control, the efficacy of the drug and/or drug coating may be reduced. Moreover, these packages tend to be heavier than desirable, they utilize more material and they require more operator handling time to pack and so are more labor intensive to produce.

BRIEF SUMMARY OF THE INVENTION

In one embodiment, the present invention is directed to a sterilizable multicompartment pouch having first and second compartments that are separated from each other by an impervious inner sheet having a breathable membrane. The breathable membrane comprises a breathable material that is pervious to moisture and gases, and impervious to liquids as well as microorganisms. The breathable membrane allows a sterilizing gas to be introduced between the first and second compartments. The front and back sheets are sealed to the inner sheet to define the first and second compartments in which the inner sheet forms a common wall between the compartments. The breathable membrane is preferably disposed towards a central portion of the inner sheet and is not present where the front and back sheets are sealed to the inner sheet. It has been discovered that by positioning the breathable material towards a central portion of the inner sheet and away from the seams forming the pouch, the ingress of moisture vapor into the pouch can be significantly reduced.

In one embodiment, an article to be sterilizable is introduced into and sealed within one of the compartments. Thereafter, a sterilizing gas can be introduced into the sealed compartment containing the article from the other compartment via the breathable membrane. An absorbent packet can then be introduced into the still open compartment, which can then be sealed when sterilization is complete. The absorbent packet may include scavengers, such as moisture and/or oxygen scavengers, that absorb moisture and gases from within the pouch. The breathable membrane permits gases/moisture that are present in the compartment containing the sterilized article to pass through the membrane and into the compartment containing the absorbent packets. As a result, moisture and gases can be removed from the adjacent compartment containing the sterilizable article without having to have the absorbent packets and the article in the same compartment.

In one embodiment, a sterilizable dual compartment pouch is provided in which front and back sheets of barrier film are arranged in opposing face-to-face relation, each having an inner surface, a top edge, a bottom edge, and opposite side edges extending longitudinally from said top edge to said bottom edge. An inner sheet of a barrier film is disposed between and connected to the front and back sheets to thereby define first and second compartments of the pouch. The inner sheet has an opening formed therein for providing communication between the first and second compartments. A breathable membrane comprising a moisture vapor permeable sheet material is disposed on the inner sheet and covers the opening. The breathable membrane includes a peripheral edge overlying the inner sheet and that is spaced from the seams forming the pouch. A continuous seam is located at or adjacent to the peripheral edge of the breathable membrane and joins the membrane to the inner sheet.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
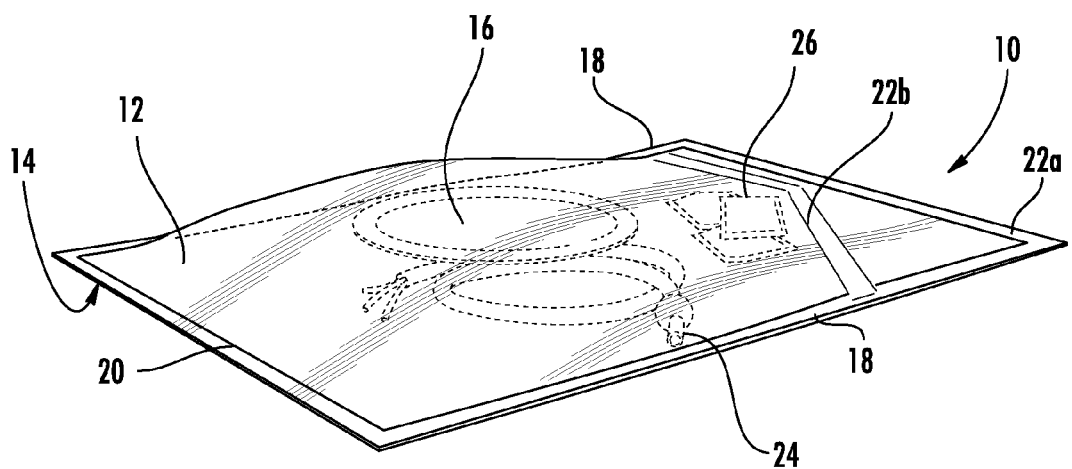
FIG. 1 is a perspective view of a dual compartment pouch that is in accordance with one embodiment of the present invention.

With reference to FIG. 1, a sterilizable dual compartment pouch in accordance with one embodiment of the present invention is illustrated and broadly designated as reference character 10. The dual compartment pouch includes front and back sheets 12, 14 that are arranged in an opposing face-to-face relationship with one another. The front and back sheets are sealed to an inner sheet (not visible in FIG. 1 but indicated at 28 in FIG. 2) to define first and second compartments in which the inner sheet forms a common wall between the compartments. The front, back and inner sheets comprise a barrier material that is impervious to liquids, gases, and microorganisms. The inner sheet 28 includes a breathable membrane 16 comprising a breathable material through which a gas, such as a sterilizing gas, can be introduced from one compartment to another to sterilize an article therein. In the illustrated embodiment, the dual compartment pouch is shown in a filled and sealed state in which the front and back sheets are sealed to the inner sheet along side seams 18, top seam 20, and bottom seams 22a, 22b, and in which a medical device 24 is disposed in the first compartment and an absorbent packet 26 is disposed in the second compartment.

Figure 2:
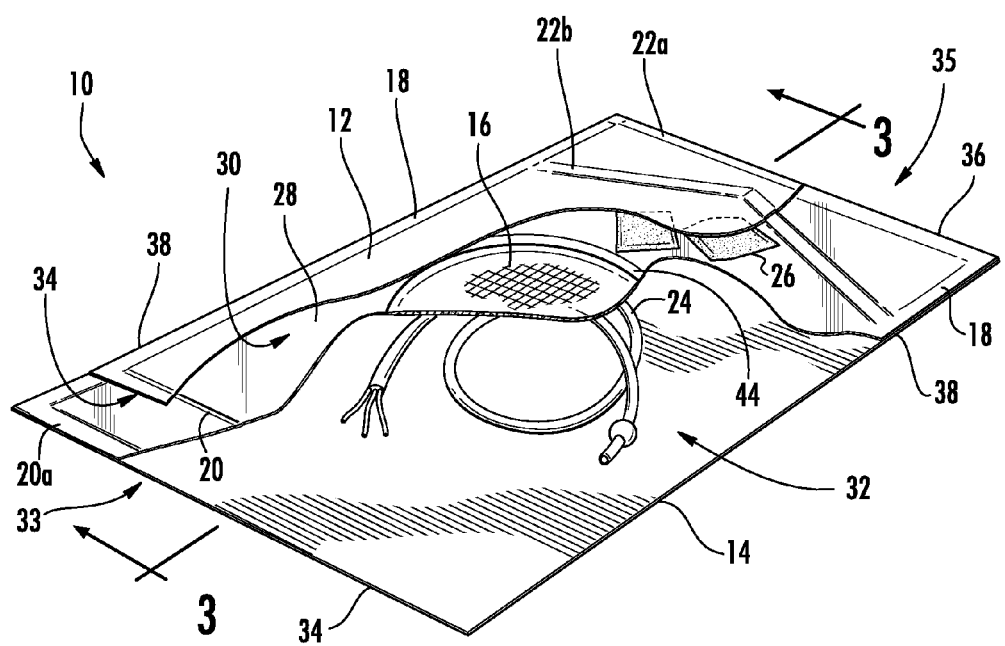
FIG. 2 is a perspective view of the pouch of FIG. 1 in which portions of the pouch are not shown to permit structural features of the pouch to be seen.
Figure 3:
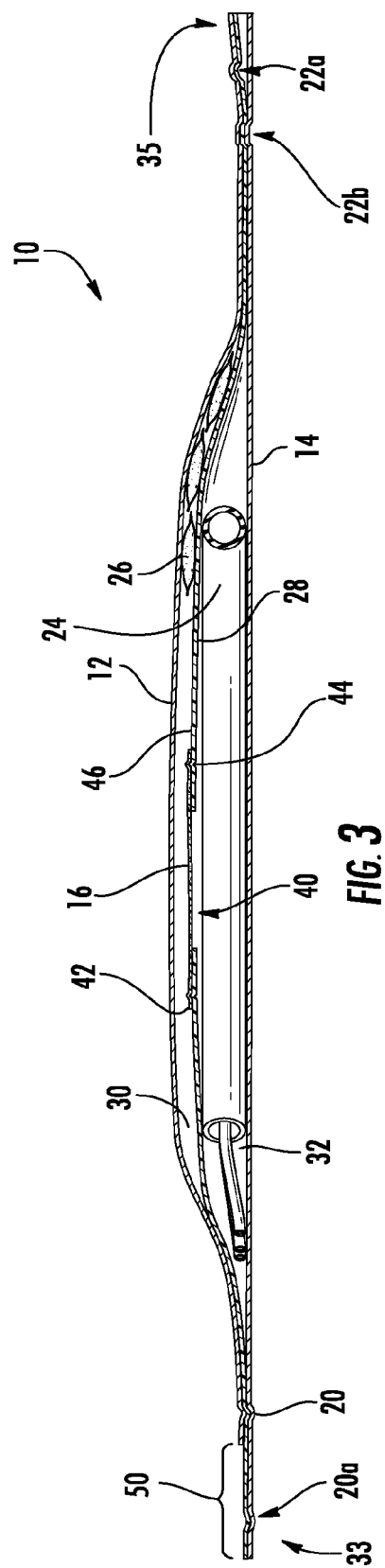
FIG. 3 is a cross-sectional side view of the pouch of FIG. 2 taken along the line 3-3 of FIG. 2.

Referring to FIGS. 2 and 3, the front and back sheets 12, 14 are disposed opposite each other with the inner sheet 28 disposed therebetween to thereby define the first and second compartments 30, 32. As shown, the first and second compartments 30, 32 are arranged in a side-by-side relation with each other with the inner sheet forming a common wall therebetween. FIG. 2 is a perspective view in which a portion of the front sheet 12 and inner sheet 28 have been partially removed so that the structure of the pouch can be seen by the reader. In the illustrated embodiment, the front, back, and inner sheets 12, 14, 28 are of a generally rectangular shape, each having a top edge 34, a bottom edge 36 and opposite side edges 38 that extend longitudinally from the top edge 34 to the bottom edge 36. The dual compartment pouch has a top end 33 and an opposite bottom end 35. In the context of the invention, the term "pouch" is used in a generic sense and should be recognized to include bags, sacks, packages, satchels and the like.

As can best be seen in FIG. 3, the inner sheet 28 includes an opening 40 for providing communication between the first and second compartments. In the illustrated embodiment, the opening has an area of about 5 to 25 percent of the area of the inner sheet. The breathable membrane 16 comprises a moisture vapor permeable, water-impermeable sheet material that is disposed on the inner sheet and covers the opening. The breathable membrane has a peripheral edge 42 that overlies the inner sheet and is spaced from the side seams and bottom seams of the pouch. In the illustrated embodiment, the opening 40 and the breathable membrane 16 are positioned towards a central portion of the inner sheet. The breathable material is joined to the surface 46 of the inner sheet along a continuous seam 44 that is located towards or adjacent to the peripheral edge 42 of the breathable membrane 16. Preferably, the breathable membrane is joined to the inner sheet with a heat seal.

The breathable membrane comprises a material that is impermeable to liquids and microorganisms, but is permeable to gases including moisture vapor, oxygen, carbon dioxide, and various sterilization gases. Preferably, the breathable membrane has a moisture vapor transmission rate (MVTR) of at least 1,000 $g/m^2/24$ hr, and more preferably at least about 1500 $g/m^2/24$ hr, and most preferably, at least about 1800 $g/m^2/24$ hr as measured according to TAPPI-T523. Suitable materials for the breathable material may include paper and nonwoven sheet materials. Suitable nonwoven sheet materials include spunbond nonwoven fabrics such as Typar® and Reemay® fabrics from Fiberweb Inc., and nonwoven fabrics formed of flash-spun polyethylene strands, such as a nonwoven sheet material sold by E.I. Du Pont de Nemours and Company under the trademark Tyvek®.

As briefly noted above, the breathable membrane is spaced away from the side seams and is not present between any of the seams (e.g., side seams 18, top seam 20a, or bottoms seams 22a, 22b) joining the front and back sheets to the inner sheet. As shown in FIG. 2, the seams forming the pouch are formed by joining the barrier material of the front, back and inner sheets to each other to provide seams having barrier properties. By positioning the breathable membrane towards a central portion of the inner sheet and away from the seams forming the pouch, the ingress of moisture vapor into the pouch can be significantly minimized. For example, the moisture vapor transmission rate through the seams forming the pouch is typically less than about 0.1 $g/100\ in^2/24$ hr/inch of seal length, and more typically less than about 0.05 $g/100\ in^2/24$ hr/inch of seal length, and most typically less than about 0.01 $g/100\ in^2/24$ hr/inch of seal length as measured according to ASTM test method F 1249. In one embodiment, the MVTR is about 0.002 $g/100\ in^2/24$ hr. for every one inch of seal length. In comparison, it is believed that a similar seam having an inner sheet composed of a nonwoven sheet material, such as Tyvek® would have a MVTR through the seam that is at least 0.39 $g/100\ in^2/24$ hr. for every for every one inch of seal length or greater, which is about 200 times greater than the MVTR that can be obtainable with an embodiment of the present invention.

Figure 4:
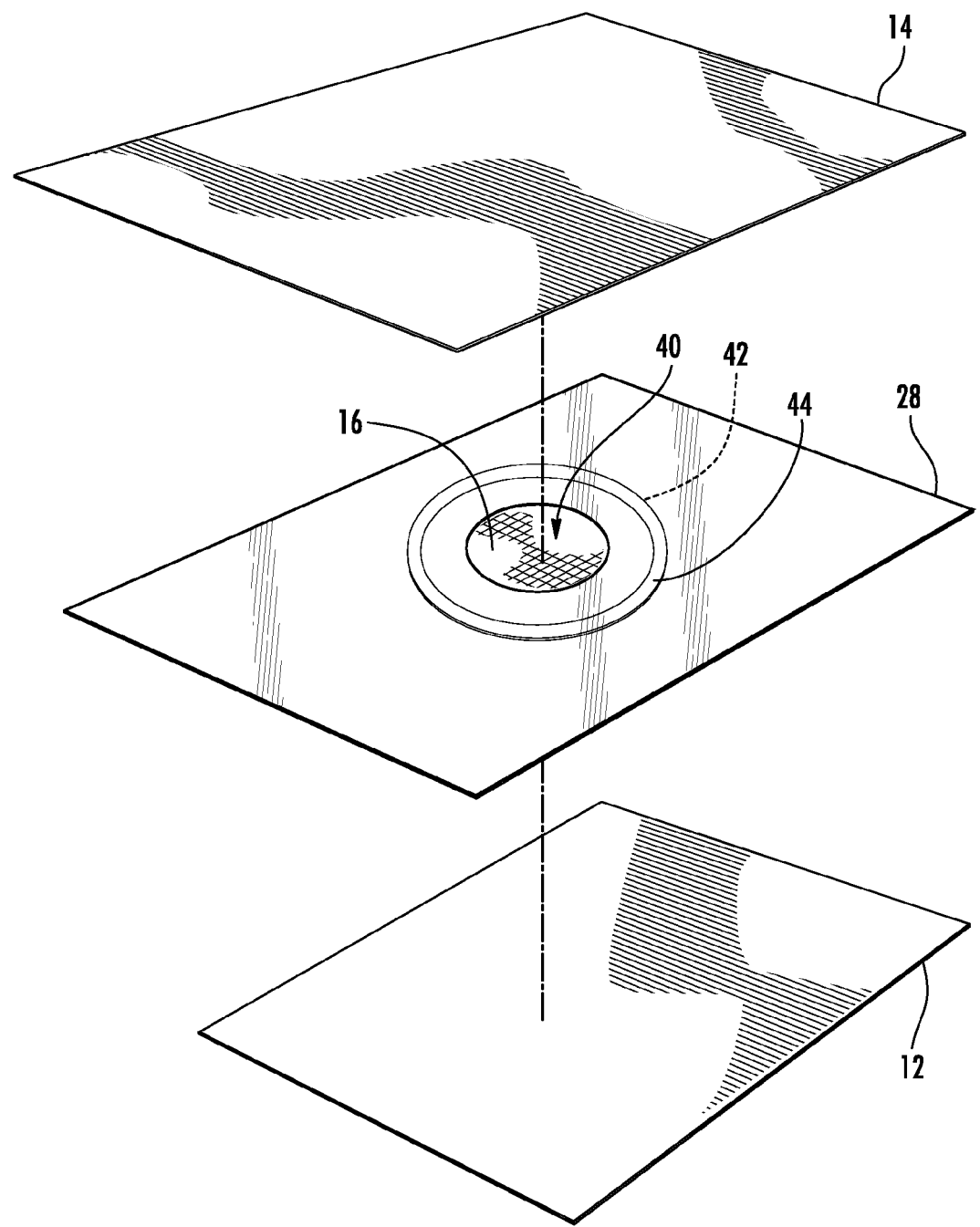
FIG. 4 is an exploded view of a pouch in accordance with one embodiment of the present invention.

FIG. 4 illustrates an exploded perspective of the dual compartment pouch 10. In this illustration, the orientation of the front, back and inner sheets has been reversed in comparison to FIGS. 1-3 so that the opening 40 formed in the inner sheet can be seen. As shown, the breathable membrane 16 is spaced apart from the edges of any one of the front, back or inner sheets. The breathable membrane has a surface area that is generally from about 10 to 60% larger than the surface area of the opening formed in the inner sheet, and in particular, from about 20 to 50% larger than the surface area of the opening formed in the inner sheet. For example, in the illustrated embodiment, the opening has a diameter that is about 3 inches, whereas the breathable membrane has a diameter that is about 5 inches. In this embodiment, the large sized breathable membrane helps to provide more freedom in the manufacturing process so that the breathable membrane does not have to be precisely positioned over the opening prior to sealing the breathable membrane to the inner sheet.

The breathable membrane generally overlies between about 10 and 90 percent of the surface area of the inner sheet. In one embodiment, the breathable membrane overlies between about 10 and 50 percent of the surface area of the inner sheet, and more typically between about 15 and 25 percent of the surface area of the inner sheet. In the figures, the inner sheet is depicted as having a single breathable membrane having a generally circular shape. However, it should be recognized that the present invention is not limited to any particular number, shape or size of the breathable membrane and that the inner sheet can include multiple breathable membranes of varying shapes and sizes.

The front and back sheets, as well as the inner sheet, comprise a flexible barrier film having liquid, moisture vapor, and gas barrier properties. Preferably, barrier films for use as the front and back sheets have an oxygen vapor transmission rate that is less than about 1 $cc/m^2/day$, and in particular less than about 0.5 $cc/m^2/day$, and more particularly less than about 0.2 $cc/m^2/day$ as measured according to ASTM test method 3985. Since the inner sheet is generally confined to the interior of the pouch, suitable barrier films for use as the inner sheet may have relatively higher oxygen transmission rates than those suitable for the front or back sheets. For example, barrier films for use as the inner sheet may have an oxygen vapor transmission rate that is less than about 100 $cc/m^2/day$, and in particular less than about 75 $cc/m^2/day$, and more particularly less than about 60 $cc/m^2/day$ as measured according to ASTM test method 3985. In the context of the invention, the term "film" may include monolayer films, multilayer films, laminates, and combinations thereof.

In one embodiment, the front, back, and inner sheets are multilayer films including one or more barrier layers composed of compositions selected to impart specific barrier properties to the film. Suitable barrier components may include metallic foil, such as aluminum foil, and metallized films, such aluminized films, aluminum oxide films (AlOx), silicon oxide films (SiOx), and films comprising polychlorotrifluoroethylene (PCTFE) such as Aclar®. The barrier films may also include polymeric components having barrier properties, such as ethylene/vinyl alcohol copolymer ("EVOH"), polyvinyl alcohol ("PVOH"), vinylidene chloride polymers ("PVdC"), polyalkylene carbonate, polyester (e.g., PET, PEN), polyacrylonitrile ("PAN"), and polyamides.

Useful polyamides may include polyamide 6, polyamide 9, polyamide 10, polyamide 11, polyamide 12, polyamide 66, polyamide 610, polyamide 612, polyamide 61, polyamide 6T, polyamide 69, copolymers made from any of the monomers used to make two or more of the foregoing homopolymers (e.g., copolyamide 6/12, polyamide 12, copolyamide 66/69/61, copolyamide 66/610, copolyamide 6/66, and copolyamide 6/69), and blends of any of the foregoing homo- and/or copolymers.

Barrier films suitable for use as the front, back, or inner sheets may include one or more additional layers that impart desired properties to the film. For example, the front, back, and inner sheets may include one or more of: outer abuse layers, sealant layers, tie layers, etc. In one embodiment, the front and back sheets include an outer abuse layer. During manufacturing, processing and shipping, the pouch, and hence the front and back sheets, may be exposed to environmental stresses, such as abrasion, high temperatures, and the like. As such, it may be desirable for the front and back sheets to include an outside or abuse layer that provides enhanced resistance to abuse. Further, since the abuse layer may be directly exposed to a heat seal bar of the heat-sealing equipment when forming the sealed pouch, the abuse layer preferably provides heat-resistant characteristics to the outer surfaces of the front and back sheets to help prevent "burn-through" during heat sealing. Suitable polymers for the abuse layer may include one or more of any of the following: polyolefins (e.g., polyethylenes, polypropylenes), polyamides, polyesters, polystyrenes, polyurethanes, and polycarbonates. Examples of suitable polyesters include amorphous (co)polyesters, poly(ethylene/terephthalic acid), and poly(ethylene/naphthalate). In a preferred embodiment, the front and back sheets include an outer abuse layer comprising polyester terephthalate.

The front and back sheets may also include a sealant layer on the opposite side of the film from the abuse layer. The sealant layer typically defines an inner surface 46 of the pouch that faces the inner sheet. The polymer material (i.e., component or blend of components) that forms the sealant layer has a melting point that facilitates heat sealing the inner surface of the front and back sheet 12, 14 to the inner sheet 28.

In one embodiment, one or more of the front and back sheets may comprise a multilayer laminate having an inner foil layer, such as aluminum foil. In this embodiment, the foil layer in addition to providing moisture and gas barrier properties also provides UV barrier properties. In a preferred embodiment, the front and back sheets comprise a laminate having an interior aluminum foil layer that is disposed between one or more polymeric layers. For example, a preferred laminate for use as the barrier film of the front or back sheets comprise a seven layer laminate having the following structure: an outer abuse layer comprising polyethylene terepthalate, a low density polyethylene layer, an inner aluminum foil layer, a nylon layer, a low density polyethylene layer and a sealant layer comprising low density polyethylene/ethylene vinyl acetate. In this embodiment, the low density polyethylene/ethylene vinyl acetate is heat sealable to the inner sheet.

Similarly, the inner sheet can comprise a multilayer film or laminate. In a preferred embodiment, the inner sheet comprises a three layer structure having an inner nylon layer that is disposed between two outer layers of polyethylene.

Referring back to FIG. 2, the front and back sheets 12, 14 are joined to the inner sheet 28 along the opposed side edges 38 by side seams 18. The side seams, as well as the other seams of the dual compartment pouch to be described presently, can be formed by any of various methods conventionally used in the packaging industry provided the seams are substantially impervious to the ingress/egress of liquids and gases. Preferably, the various seams are substantially impervious to gases such as moisture vapor, oxygen, carbon dioxide, etc. Suitable methods for forming the seams may include adhesive or fusion bonding, such as by forming seals with heat or ultrasonic energy. In the particular embodiment illustrated, the front, back, and inner sheets are made from a heat sealable material and the various seams are formed by producing a fusion bond or seal between contacting interior surfaces of the front and back sheets to the inner sheet using pressure and heat or ultrasonic energy as is well known. Although referred to herein as "heat seals", it should be understood that this term is intended to apply both to seals formed by heating the contacting surfaces with a heated anvil or platen, as well as to heating and fusion produced by other methods, such as application of ultrasonic energy.

In one embodiment, the second compartment 32 includes a peelable or frangible seal that can be relatively easily broken to permit a user to gain access to an article disposed therein. In this regard, FIGS. 2 and 3 illustrate an embodiment of the invention in which the front sheet and inner sheet are sealed to each other with a non-frangible or permanent seal 22a, and the back sheet and inner sheet are sealed to each other with only a frangible seal 22b. As used herein, the term frangible seal includes a seal which is sufficiently durable to allow normal handling and sterilizing of the pouch yet which will peel or substantially separate under pressure applied by pulling the back sheet away from the inner sheet. By providing the first compartment with a non-frangible seal and the second compartment with a frangible seal, the pouch can be torn open to remove the article from within the second compartment with out breaching the first compartment. In some embodiments, the pouch may not include a frangible seal. In such embodiments, the front sheet, back sheet, and inner sheet can be heat sealed to each other along their respective bottom edges.

The bottom frangible seal 22b typically has a peel strength that is from about 1 lb./in. to 4 lb/in., and more typically from about 1.5 to 4 lbs./in. In one embodiment, the frangible seal has a peel strength that is from about 2 to 3 lbs./in. Preferably the bottom frangible seal has a peel strength that is no less than about 1 lb./in. as measured by ASTM test F88. Preferably, each of the side seals 18, bottom seal 22a, and top seal 20 are non-frangible and are permanently sealed and will not rupture by the force necessary to break the frangible seal. Typically, the seal strength for non-frangible seals is about 6 or greater as measured by ASTM test F88.

Figure 5:
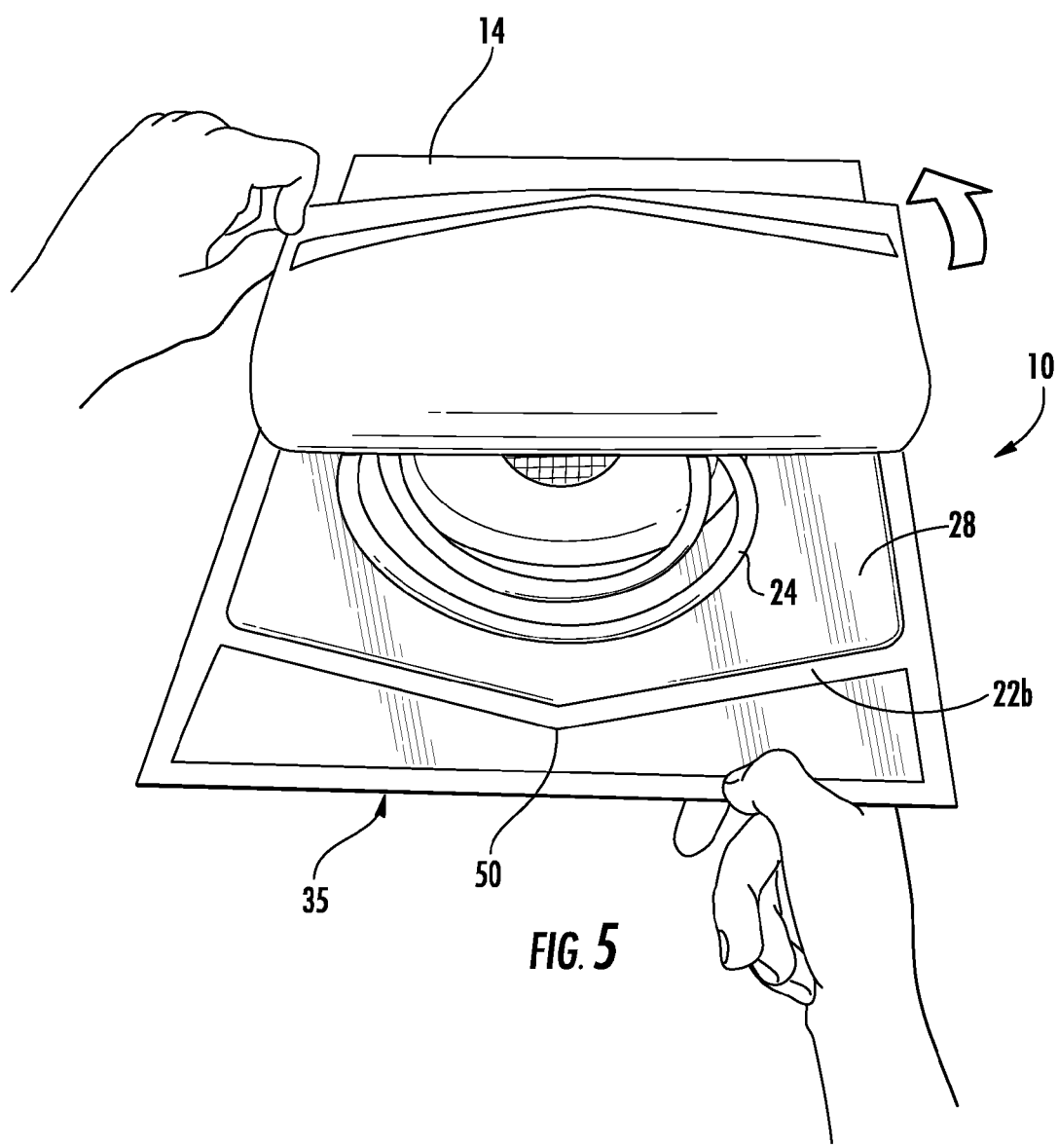
FIG. 5 is an illustration depicting a person opening the pouch to remove a device disposed therein.

As can best be seen in FIG. 3, the bottom end 35 of the second compartment 32 includes a non-frangible seal 22a between the front sheet and inner sheet, whereas such a seal is not present between the back and inner sheets. Rather, the second compartment includes a frangible seal 22b that permits a user to break the frangible seal and thereby open the second compartment at a desired time by simply pulling the back sheet away from the inner sheet. In this regard, FIG. 5 illustrates the second compartment 32 in the process of being opened by breaking the frangible seal 22b, for example, by pulling the back sheet away from the inner sheet. In a preferred embodiment, the side seams joining the front sheet to the inner sheet are also frangible to assist in peeling the back sheet away from the inner sheet, whereas the side seams joining the front sheet to the inner sheet are non-frangible.

Generally, the strength of a seal, and hence, frangibility, is a function of the amount of heat and pressure that is applied over a given time in making the seal. Thus, a relatively weak seal can be created by decreasing one or more of the temperature, pressure and dwell time at which the seal is created. Additionally, the shape of the seal can also be configured to aid in its frangibility. In this regard, the FIGS. illustrate an embodiment of the invention in which the frangible seal has a "chevron-like" shape. In the illustrated embodiment, the frangible seal has a chevron-like shape in which an apex 50 of the frangible seal 22b is facing towards the bottom edges of the back and inner sheets. As shown in FIG. 5, as the back sheet is pulled away from the inner sheet only a portion of the frangible seal at any given time is being pulled apart. As a result, the amount of force necessary to break the frangible seal is spread out over the length of the seal as it is pulled apart. This allows a seal having a greater strength to be used without having to sacrifice the frangibility of the seals. In other words, the amount of force applied to one area of the frangible force can be reduced to effect rupture of the frangible seal in comparison to a seal that extends laterally between opposing side seams of the pouch (e.g., bottom seam 22a).

In one embodiment, the frangible seal 22b is spaced apart from the bottom edges of the sheets and towards the interior of the bag. Spacing the frangible seal away from the edges may help assist in opening the bag by providing a user a portion of the back sheet that can be easily gripped for pulling the back sheet away from the inner sheet. In one embodiment, the frangible seal is spaced about 0.5 to 4 inches away from the bottom edges of the sheets, and more typically between about 1 and 3 inches.

In the embodiment illustrated in FIGS. 2 and 3, the top edges of the back and inner sheets 14, 28 extend beyond the top edge of the front sheet 12. As a result, a portion 50 of the second compartment 32 extends beyond the top edge of the front sheet, and hence, beyond the opening of the first compartment 30. Generally, prior to introducing articles into the compartments and forming any one of seams forming the pouch, the top edges of each of the sheets are relatively unconnected to each other to thereby define openings for each compartment (see briefly FIG. 6, reference numbers 62, 64). As discussed in greater detail below, the openings to each compartment permit article(s) to be introduced into the interior of each compartment. Further, the opening to the front compartment also provides a means for introducing a sterilizing gas into the pouch. After an article has been introduced into the second compartment 32, the back sheet and inner sheet can be sealed to each other along their respective top edges to produce top seal 20a. Since this portion of the pouch extends beyond the front sheet 12, the opening to the first compartment is unaffected by the creation of top seal 20a. In a subsequent step, the first compartment 30 can be filled and the inner sheet can be heat sealed to the back sheet along the top edge of the front sheet to form top seal 20. As can best be seen in FIG. 3, the creation of the top seal between the inner sheet and the front sheet typically seals both the back and front sheets to the inner sheet.

The dual compartment pouch of the present invention may be prepared from a variety of suitable plastic materials whereby a strong, lightweight, reliable, yet economic container is provided. Preferably, each sheet comprises a plastic material having an inner surface capable of forming a strong heat seal with the opposing surfaces of the inner sheet to define the pouch. Additionally, pouches for use in medical applications are generally formed from sheet material having both moisture barrier properties and gas barrier properties. In one embodiment, the sealed pouch has a moisture vapor transmission rate that is less than about 0.1 g/100 in$^2$/day, and in particular less than about 0.05 g/100 in$^2$/day, and more particularly less than about 0.01 g/100 in$^2$/day as measured according to ASTM test method F1249. In a further embodiment, the pouch has an $O_2$ transmission rate that is less than about 0.01 cc/100 in$^2$/day, and in particular, less than about 0.5 cc/100 in$^2$/day as measured according to ASTM test method F1249 Unless otherwise stated all measurements of $O_2$ transmission rate are measured according to ASTM test method F1249.

Figure 6:
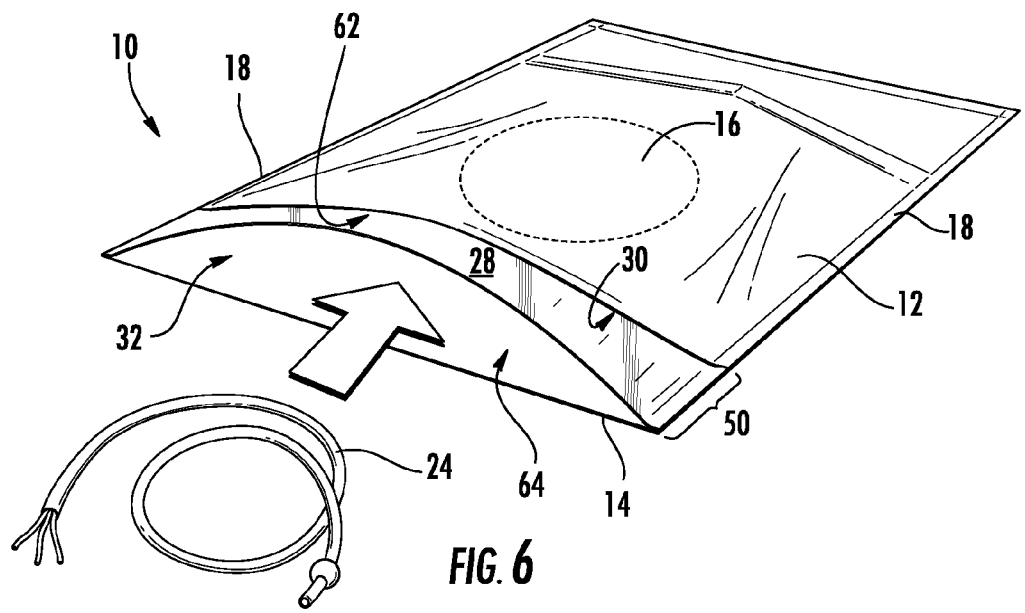
FIGS. 6 through 11 illustrate in a step-wise manner a process of filling and sealing a pouch that is in accordance with one embodiment of the invention.
Figure 7:
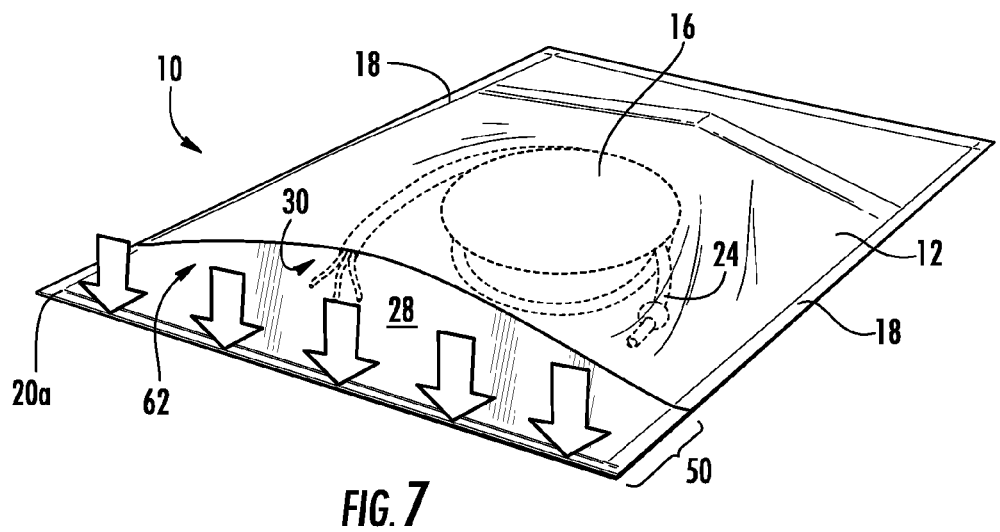

With reference to FIGS. 6-11, an exemplary process of using a dual compartment pouch that is in accordance with one embodiment of the invention is shown. In FIG. 6, an open and unfilled pouch 10 that is in accordance with the present invention is provided. As shown, the top edges of the front, back, and inner sheets are unconnected to each other to define openings 62, 64 into the first and second compartments 30, 32, respectively. In the first step, an article 24, such as a stent and an associated delivery system, is introduced into the second compartment of the pouch through opening 64. As shown in FIG. 7, the top edges of the inner sheet and back sheet are heat sealed to each other to form seal 20a and thereby sealably close the opening to the second compartment. In some embodiments, a vacuum can be applied to the second compartment prior to sealing the opening to remove any residual oxygen or gas.

Figure 8:
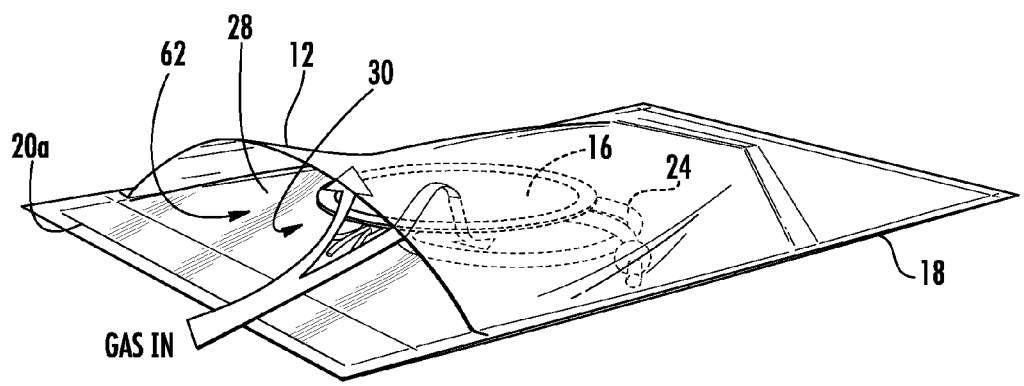
Figure 9:
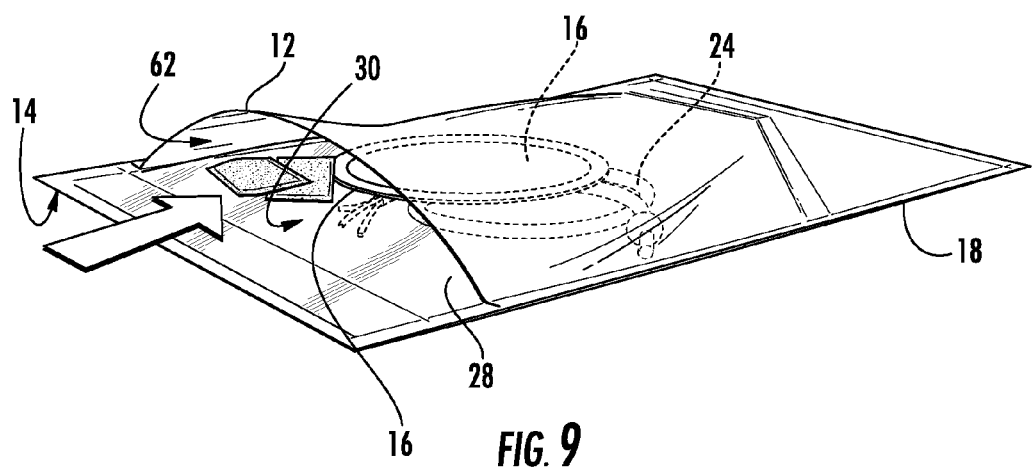

As shown in FIG. 8, a sterilizing gas is then introduced into the first compartment 30 through opening 62. As the sterilizing gas, such as ethylene oxide, is introduced into the first compartment, it flows through the breathable membrane 16 and into the second compartment. The sterilizing gas is introduced into the pouch for a sufficient amount of time so that the article is sterilized. As shown in FIG. 9, absorbent packets 26 are introduced into the first compartment. Preferably, the absorbent packets are not introduced into the pouch until the step of introducing sterilizing gas is completed. The absorbent packets may include one or more of moisture desiccants, oxygen scavengers, carbon dioxide scavengers, and the like. Typical moisture desiccants may include silica gel packets, molecular sieves, calcium chloride, and the like.

Figure 10:
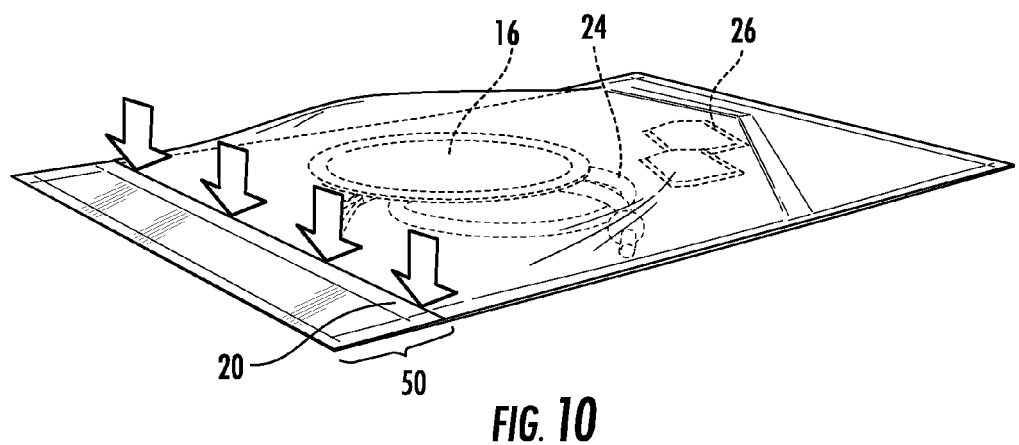
Figure 11:
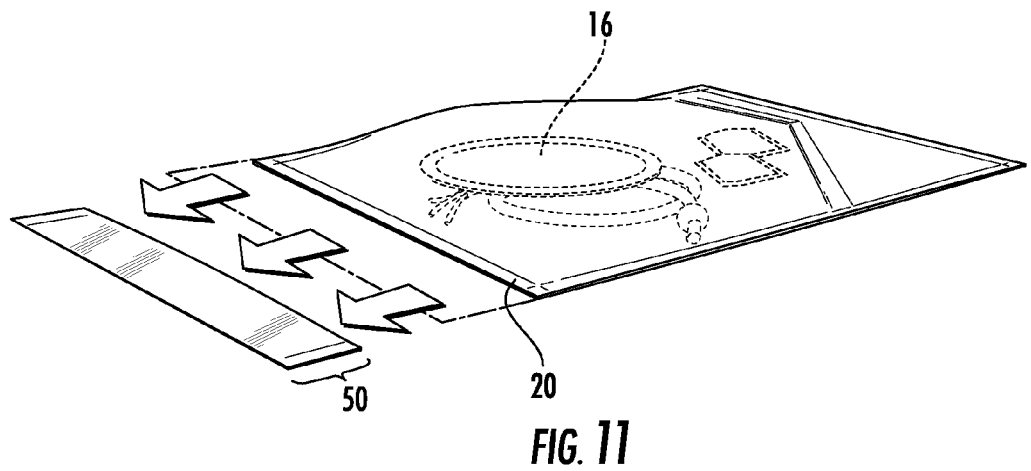

In FIG. 10, the inner front and inner sheets are sealed to each other to close opening 62 and thereby seal the absorbing packets in the first compartment. As shown in FIG. 11, the portion 50 of the second compartment extending beyond the top seal 20 can be trimmed away to provide a packaged article having a clean appearance. After sealing the openings to the pouch, the absorbent packets will absorb moisture and other gases in the pouch to provide a controlled sterile environment for the article packaged therein. In particular, the absorbent packets can draw moisture from the second compartment through the breathable membrane. As a result, the absorbent packets can protect the packaged article without having any physical contact.

In some embodiments, the first and second compartments are flushed with an inert gas, such as nitrogen, prior to being filled. Additionally, a vacuum can also be applied to the first and second compartments prior to sealing.

Dual compartment pouches in accordance with the present invention can be prepared utilizing various processing procedures. In one embodiment, the pouch is prepared in a multi-step process in which the back sheet and inner sheet are superimposed and heat sealed to each other to form the second compartment along their adjacent bottom edges. Next, the front sheet is superimposed over the second compartment opposite the inner sheet. The front and back sheets are then sealed to the inner sheet along the opposing side edges to form the side seams. In embodiments having a frangible seal, the front sheet is sealed to the inner sheet to form a frangible seal towards the bottom end of the pouch. In some embodiments, the heat seal forming the frangible seal will also be present between the back sheet and the inner sheet (see briefly, FIG. 3). The thus completed pouch includes first and second compartments that are joined together along side seams and bottom seams. The top edges of the front, back and inner sheets are unconnected to each other to define openings through which articles can be introduced into the interior of each compartment. It should be recognized that the above described process can be set up for automation utilizing a variety of different machinery.

As should be evident from the foregoing discussion, the present invention can be used to package a wide variety of different items in which it is desirable to minimize contact with oxygen, moisture, and absorbent packets. In one particular embodiment, the present invention can be used to package a wide variety of medical devices including catheters, stents, and in particular drug coated stents.

EXAMPLES

A dual compartment pouch was prepared in accordance with the present invention. The pouch was prepared from a front sheet, inner sheet, and back sheet that were heat sealed to each other about their peripheral edges to form the dual compartment pouch. The sheets had the following structure:

The front and back sheets were each composed of seven layers in the following order:
  48 gauge polyethylene terephthalate (PET)
  low density polyethylene (LDPE)
  70 gauge Aluminum Foil
  low density polyethylene (LDPE)
  60 gauge nylon
  low density polyethylene (LDPE)
  2 mil low density polyethylene/ethylene vinyl acetate (EVA)

TABLE 1

Properties of the Front and Back Sheets

| TECHNICAL DATA PROPERTY | VALUE | METHOD |
|---|---|---|
| Thickness | 160 μm | ASTM D645 |
| Basis Weight | 186.3 g/m$^2$ | TAPPI T410 |
| Yield | 5.36 m$^2$/kg | TAPPI T410 |
| Tensile Strength (film) | | ASTM D882 |
| MD | 65.7 MPa | |
| TD | 57.2 MPa | |
| Percent Elongation at Break | | ASTM D882 |
| MD | 112% | |
| TD | 104% | |
| Puncture Strength (⅛" Probe) | 128N | ASTM F1306 |
| Seal Strength (to itself, 375° F., 50 Psi, 1 sec dwell, 90° Tail) | Destruct N/15 mm | ASTM F88 |
| WVTR | <0.16 g/m$^2$/day | ASTM F1249 |
| O$_2$TR | <0.16 cc/m$^2$/day | ASTM 3985 |

The inner sheet was three layer composite film with the following layers:
  Polyethylene;
  Nylon; and
  Polyethylene

TABLE 2

Properties of the Inner Sheet

| TECHNICAL DATA PROPERTY | VALUE | METHOD |
|---|---|---|
| Thickness | 102 μm | ASTM D645 |
| Yield | 10.23 m$^2$/kg | TAPPI T410 |
| Tensile Strength (film) | | ASTM D882 |
| MD | 36.18 MPa | |
| TD | 32.00 MPa | |
| Tensile Load at Break | | ASTM D882 |
| MD | 55.43 N/15 mm | |
| TD | 48.50 N/15 mm | |
| Percent Elongation at Break | | ASTM D882 |
| MD | 610% | |
| TD | 660% | |
| Yield Strength | | ASTM D882 |
| MD | 16.70 MPa | |
| TD | 17.40 MPa | |
| Secant Modulus | | ASTM D882 |
| MD | 380 000 KPa | |
| TD | 440 000 KPa | |
| Tear Strength (Elmendorf) | | ASTM D1922 |
| MD | 2600 mN | |
| TD | 4500 mN | |
| Puncture Strength (⅛" Probe) | 44.5 N | FTMS 101C |
| Impact Strength (Dynatup) | 58.3 N | ASTM D5628 |
| Kinetic Coefficient of Friction | | ASTM D1894 |
| Outer/Outer | 0.35 | |
| Seal/Seal | 0.25 | |
| Gelbo Flex (Pinhole Resistance) (1000 cycles) | 8.5 Pinholes | MIL STD 105 |
| Gloss (60°) | 98% | ASTM D2457 |
| Haze | 18% | ASTM D1003 |
| WVTR | 6.2 g/m$^2$/24 hrs | ASTM F1249 |
| O$_2$TR | 59 cc/m$^2$/24 hrs | ASTM 3985 |

A dual compartment pouch in accordance with one embodiment of the invention was then assembled by superimposing an inner sheet of the above described barrier film over a front sheet barrier film described above. The inner sheet included an opening and a breathable material covering the opening and sealed to a surface of the inner sheet. The inner and front sheets were sealed to each other along their respective side edges and bottom edges to produce opposing side seams and a bottom seam having a peel strength of about 13 lbs./in. Next, a back sheet was superimposed over the surface of the inner sheet. A peelable (frangible) heat seal having a chevron shape was created between the back sheet and the inner sheet towards the bottom end of the pouch. A pair of opposing peelable (frangible) heat seals were created on opposite side edges of the pouch to join the and back sheet to the inner sheet. The peelable (frangible) side seams and bottom seam between the back and inner sheets had a peel strength of about 3.9 lbs./in.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A dual compartment pouch comprising:
   front and back sheets of a flexible barrier film arranged in opposing face-to-face relation, each having an inner surface, a top edge, a bottom edge, and opposite side edges extending longitudinally from said top edge to said bottom edge;
   an inner sheet of a flexible barrier film disposed between the front and back sheets and having a top edge, a bottom edge, and opposite side edges, the inner sheet defining first and second compartments within the pouch;
   side seams extending longitudinally along said opposite side edges and joining the front and back sheets to the inner sheet;
   a bottom seam extending transversely along said bottom edges and joining the front and back sheets to the inner sheet;
   an opening formed in the inner sheet and providing communication between the first and second compartments;
   a breathable membrane disposed on the inner sheet and covering said opening, said breathable membrane having a peripheral edge overlying the inner sheet and spaced from said side seams and bottom seam, the breathable membrane comprising a moisture vapor permeable, water-impermeable sheet material; and
   a seam located at or adjacent the peripheral edge of the breathable membrane joining the membrane to the inner sheet.

2. The pouch of claim 1, wherein the breathable membrane comprises paper or a nonwoven fabric.

3. The pouch of claim 1, wherein the barrier film of the inner sheet includes a heat sealable thermoplastic material on opposite surfaces.

4. The pouch of claim 1, wherein the top edge of the inner sheet is unconnected to the front sheet or the back sheet to define access openings into the first and second compartments.

5. The pouch of claim 1, further comprising a frangible seal disposed between the front sheet and the inner sheet towards a bottom end of the pouch.

6. The pouch of claim 4, wherein the frangible seal has a peel strength that is from about 2 to 4 lbs./in.

7. The pouch of claim 4, wherein the frangible seal has a chevron shape with an apex directed towards the bottom edges of the back and inner sheets.

8. The pouch of claim 1, wherein the moisture vapor transmission rate through any one of the seams is less than about 0.1 g/100 in$^2$/24 hr/inch of seal length.

9. The pouch of claim 1, wherein the opening in the inner sheet covers about 5 to 25% of the surface area of the inner sheet.

10. The pouch of claim 1, wherein the inner sheet has a surface and the breathable membrane covers about 10 to 50 percent of the surface of the inner sheet.

11. The pouch of claim 1, wherein the breathable membrane has a surface area that is about 10 to 60% larger than the surface area of said opening.

12. The pouch of claim 1, wherein the top edges of the inner sheet and the back sheet extend beyond the top edge of the front sheet.

13. The pouch of claim 1, wherein the opening in the inner sheet and the breathable membrane are circular, and are joined to each other by a continuous seam that is located at or adjacent the peripheral edge of the breathable membrane.

14. A sterilizable dual compartment pouch comprising:
    front and back sheets of a flexible barrier film arranged in opposing face-to-face relation, each having an inner surface, a top edge, a bottom edge, and opposite side edges extending longitudinally from said top edge to said bottom edge;
    an inner sheet of a flexible barrier film disposed between the front and back sheets and having a top edge, a bottom edge, and opposite side edges, the inner sheet defining first and second compartments within the pouch;
    side seams extending longitudinally along said opposite side edges and joining the front and back sheets to the inner sheet;
    a bottom seam extending transversely along said bottom edges and joining the front and back sheets to the inner sheet;
    a top seam extending transversely along said top edges and joining the front and back sheets to the inner sheet and
    an opening formed in the inner sheet and providing communication between the first and second compartments;
    a breathable membrane disposed on the inner sheet and covering said opening, said breathable membrane having a peripheral edge overlying the inner sheet and spaced from said side seams, top seam, and bottom seam, the breathable membrane comprising a moisture vapor permeable, water-impermeable sheet material; and
    a continuous seam located at or adjacent the peripheral edge of the breathable membrane joining the membrane to the inner sheet.

15. The sterilizable dual compartment pouch of claim 14, further comprising a medical device disposed in the second compartment.

16. The sterilizable dual compartment pouch of claim 15, wherein the medical device is a stent that is coated with a therapeutic drug agent.

17. The sterilizable dual compartment pouch of claim 14, further comprising one or more of a desiccant or scavenging agent disposed in the first compartment.

18. The sterilizable dual compartment pouch of claim 14, wherein the front and back sheets include an aluminum foil layer and wherein the inner sheet comprises nylon.

19. The sterilizable dual compartment pouch of claim 14, wherein the side seam, bottom seam, and top seam have a moisture vapor transmission rate that is less than about 0.05 g/100 in$^2$/24 hr/inch of seal length.

20. A method of sterilizing an article comprising
providing the pouch of claim 1;
introducing an article into the second compartment;
sealing the top edges of the inner sheet and the back sheet to each other;
introducing a sterilizing gas into the first compartment;
passing the sterilizing gas from the first compartment to the second compartment via the breathable membrane;
introducing one or more absorbents into the first compartment; and
sealing the top edge of the front sheet to the inner sheet.

21. The method of claim 20, further comprising the step of flushing the first and second compartments with an inert gas prior to the introduction of one or more absorbents.

22. The method of claim 20, wherein the pouch has a moisture vapor transmission rate that is less than about 0.05 g/100 in$^2$/24 hr/inch of seal length.

23. The method of claim 20, wherein the article is a stent that is coated with a therapeutic drug agent.

24. The method of claim 20, wherein the breathable membrane comprises paper or a nonwoven.

* * * * *